United States Patent [19]
Jack et al.

[11] Patent Number: 5,294,440
[45] Date of Patent: Mar. 15, 1994

[54] COMPOSITION FOR TREATMENT OF COLD SORES

[75] Inventors: Bruce A. Jack; B. Thomas White, both of Albuquerque, N. Mex.

[73] Assignee: Professional Pharmaceutical Inc., Albuquerque, N. Mex.

[21] Appl. No.: 886,304

[22] Filed: May 21, 1992

Related U.S. Application Data

[63] Continuation of Ser. No. 715,410, Jun. 14, 1991, abandoned.

[51] Int. Cl.$^5$ .............................................. A61K 31/13
[52] U.S. Cl. .......................... 424/78.05; 424/78.24; 514/400; 514/944
[58] Field of Search .................. 424/401, 78.24, 78.05; 514/400, 944

[56] References Cited

U.S. PATENT DOCUMENTS

| | | | |
|---|---|---|---|
| 4,540,572 | 9/1985 | Seth | 424/81 |
| 4,618,490 | 10/1986 | De Marco | 424/80 |
| 4,966,892 | 10/1990 | McAnalley | 536/102 |

OTHER PUBLICATIONS

"Inflamation and the Function of leukocytes", Textbook of Medicl Physiology. pp. 72-73 and 86.
"The Pharmacological Basis of Therapeutics", by Louis S. Goodman and Alfred Gilman, Fifth Edition, pp. 595-600, (Chap. 29).

Primary Examiner—Thurman K. Page
Assistant Examiner—Raj Bawa
Attorney, Agent, or Firm—Cahill, Sutton & Thomas

[57] ABSTRACT

A pharmaceutical composition of water, water soluble vinyl polymer gel, amine alcohol dispersant and 1H-imidazole-4-ethanamine, phosphate (IEP) is used topically to treat herpes labialis lesions.

4 Claims, No Drawings

COMPOSITION FOR TREATMENT OF COLD SORES

This is a continuation of patent application Ser. No. 715,410, filed Jun. 14, 1991, now abandoned, by Bruce A. Jack et al., and entitled "COMPOSITION FOR TREATMENT OF COLD SORES AND THE LIKE".

BACKGROUND OF THE INVENTION

The invention relates to compositions and methods for treatment of cold sores or fever blisters, and canker sores, herpes labialis and aphthous stomatitis lesions.

There are a number of over-the-counter medications for cold sores, fever blisters and the like, including BLISTEX, ZILACTIN, and CAMPHO PHENIQUE. A prescription medication also is available, under the trademark ZOVIRAX. However, for many persons suffering from cold sores, fever blisters, etc., none of these medications is very effective.

Histamine phosphate previously has been used as a diagnostic agent for determining how much acid the human stomach produces. Histamine phosphate also has been used for injection in human skin to cause a flare-up reaction indicative of the ability of certain drugs to inhibit histamine-induced wheals, thereby indicating clinical response in allergenic diseases.

The histamine phosphate referred to is the compound 1H-imidazole-4-ethanamine phosphate (IEP), and is currently used in subcutaneous injection for the diagnosis of gastric function. Principal effects of IEP from subcutaneous, intramuscular or intravenous administration occur on the vascular system, smooth muscles, and exocrine glands. In humans, IEP produces vasodilation in the small blood vessels and capillaries causing a flushing of the face, reduction in systemic blood pressure, increase in skin temperature, and increased capillary permeability sufficient to produce exudation of fluid, plasma proteins, and erythrocytes into extracellular spaces.

Intracutaneous injection of 0.01-0.02 milligrams of IEP can create a characteristic "triple response" including a reddening at the site of the injection, a wheal or patch of localized edema within 20-60 seconds, followed by a bright halo or a flare around the wheal.

There is considerable species variation with regard to the response of smooth muscles to IEP. In humans, IEP stimulates smooth muscle contraction of the gastrointestinal (GI) tract, contraction of the sphincter of Oddi and bile duct, and potent bronchoconstriction in patients with bronchial asthma, emphysema, or bronchitis. IEP has little effect on the smooth muscle of the uterus and has little bronchoconstrictor effect on healthy individuals.

IEP is metabolized in the liver by methylation and oxidation, and the metabolites are excreted in the urine. IEP is largely inactive when given by mouth. No information has been found regarding the extent of systemic absorption following topical administration of IEP. It has been suggested by Kahlson et al. that exogenous IEP might play a beneficial role in the healing process of certain types of tissue damage. The CARBOPOL gel base is widely used in the cosmetic industry and has been proven safe.

Recurrent herpes simplex stomatitis may occur on the lips or intraorally. Outbreaks may be associated with trauma, fatigue, menstrual cycle, emotional upset, or exposure to sunlight. Vesicles, or intraepithelial blisters, usually are preceded by burning, swelling and soreness in the area where lesions subsequently develop. Vesicles are small, 1 millimeter in diameter or less, and may coalesce to form larger lesions. These vesicles rupture quickly, leaving small ulcerations. The most common sites of recurrent intraora lesions are the hard palate and attached gingiva. Lesions gradually heal within 7-10 days producing no scarring.

Canker sore lesions are characterized by the development of painful, recurring necrotizing ulcerations of the oral mucosa either as solitary or multiple lesions. Etiology is unclear; however, considerable evidence suggests the disease may be an immunologic hypersensitivity response to an L-form streptococcus bacterium. Precipitating factors in canker sore lesions may include trauma (dental procedures), self-inflicted bites (as in eating), endocrine changes (premenstrual periods, following childbirth, menopause), acute psychological problems (period of increased stress), and allergic responses (asthma, eating certain foods or taking certain medications).

The aphthous ulcer can begin as a single or a multiple superficial erosion covered by a gray membrane. The most common sites of occurrence are the mucosa of the lips and cheeks, soft palate, tongue, pharynx, and all locations of unattached (to bone) gingiva and mucosa. The ulcers persist for 7 to 10 days and heal gradually producing no scarring.

There is an unmet need for an effective remedy for fever blisters, cold sores, canker sores, gum ulcers, etc.

SUMMARY OF THE INVENTION

It is an object of the invention to provide improved medication and treatment for herpes labialis and aphthous stomatitis lesions, i.e., for fever blisters, cold sores and canker sores, and the like.

It is another object of the invention to provide a medication for treatment of herpes labialis and aphthous stomatitis lesions having the highest concentration possible without producing damaging local tissue responses.

It is another object of the invention to provide a medication of the type described that is odorless, tasteless, and leaves no residue when it dries.

It is another object of the invention to provide a composition for treatment for herpes labialis and aphthous stomatitis lesions which can stop progression of the lesion in any phase of its development.

Briefly described and in accordance with one embodiment thereof, the invention provides a composition and method of use for topical treatment of skin lesions for herpes labialis and aphthous stomatitis lesions, e.g., such as cold sores, canker sores, herpes lesions, and the like. The preparation includes a water soluble vinyl polymer gel base, such as CARBOPOL 940 mixed uniformly with water, a dispensing agent and histamine phosphate 1H-imidazole-4-ethanamine, phosphate (IEP). In the described embodiment, IEP may constitute from less than one percent to four percent of the total formulation. The preparation is applied topically to the forming or formed lesion four to five times a day.

DETAILED DESCRIPTION OF A PREFERRED EMBODIMENT OF THE INVENTION

In accordance with the present invention, a new formulation has been discovered which, when applied topically to herpes labialis and aphthous stomatitis lesions, has been found to be very effective in either preventing lesions from occurring or mitigating the duration and pain from such lesions already developed. Preliminary evaluation indicates that if the medication of the present invention is applied initially when symptoms of a cold sore lesion are first developing (when numbness, prickling sensation, etc. are experienced), subsequent phases of the lesion do not develop.

TABLE 1-continued

|  | DISEASE STATE | |
|---|---|---|
|  | HERPES LABIALIS | APHTHOUS STOMATITIS |
| needed to eliminate clinical symptoms |  |  |

TABLE 2

|  | DISEASE STATE | | | |
|---|---|---|---|---|
|  | HERPES LABIALIS REDUCTION AFTER | | APHTHOUS STOMATITIS REDUCTION AFTER | |
| CLINICAL SYMPTOM OR SIGN | 1 APPLICATION | 1 DAY | 1 APPLICATION | 1 DAY |
| Pain | 58% | 87% | 73% | 80% |
| Burning | 63% | 92% | 20% | 40% |
| Itching | 60% | 97% | none reported | |
| Swelling | 27% | 72% | 20% | 50% |
| Size (of lesion) | 10% | 32% | 23% | 43% |
| Spreading (of lesion) | 40% | 62% | none reported | |

EXAMPLE

The composition of the present invention includes initial preparation of a gel base by adding 0.8% CARBOPOL 940, which is a vinyl polymer, to distilled water. This mixture was allowed to stand for several hours until the polymer was wetted and a gel was formed. This mixture then was blended by means of a ordinary high speed mixer, such as a Lightning Labmaster II until a homogenous mixture is formed. At this point, a dispensing agent such as an amino alcohol was added, forming an emulsion. Then, IEP totaling 0.0067 percent by weight of the total formulation was added to the gel and blended until a homogenous composition was obtained. This composition then was applied topically to various types of lesions, as subsequently described.

The present invention was used by fifty to sixty patients exhibiting herpetic stomatitis lesions (fever blisters or cold sores) and three patients with aphthous ulcers (canker sores). Treatment consisted of topical application of the medication four to five times a day at the lesion sites.

All patients experienced a decrease in healing time compared to an untreated episode. Table 1 shows the results for nine of the patients Data was gathered from the other patients on a more informal basis, but all reported great improvement over the results of using other medications. Approximately two-thirds of the total patients in both treatment groups experienced the abortion of lesions, that is, when the medication was applied at the time of the first sensation of burning, tautness or swelling, no lesion developed.

Table 2 data show the reduction of clinical symptoms or signs for the same nine patients after one application and after one day of treatment, including the reduction in both size and spreading of lesions. All patients experienced a decrease in clinical symptoms and in the size of the lesions developed, beginning with the initial treatment.

TABLE 1

|  | DISEASE STATE | |
|---|---|---|
|  | HERPES LABIALIS | APHTHOUS STOMATITIS |
| Percentage decrease in healing time compared to untreated episode | 49% | 67% |
| Percentage of patients who experienced lesion abortion | 60% | 67% |
| Estimated number of applications | 5 | 9 |

DISCUSSION

As the above observations indicate, the preparation as described is effective in treating fever blisters and canker sores There were no side effects or adverse reactions reported by any patient.

Concentrations of IEP from approximately 0.00325 percent to 0.0067 percent, represent dosage levels far less than the dosage levels when IEP has been given systemically in the prior art, and from 6 to 50 times less than when given intradermally in the prior art. Since IEP is largely inactivated when ingested, no adverse effects are anticipated from topical applications. The above indicated level of IEP, namely 0.0067 percent by weight, represents what we presently believe to be a near optimum concentration of IEP. Informal initial testing (on other than the above-mentioned fifty to sixty patients) were performed at IEP concentrations of 0.00325 percent by weight. These results produced positive results, but not nearly as good as results obtained by doubling that concentration of IEP. Based on the pharmacology of IEP, we suspect that substantial further increases in the concentration of IEP may lead to adverse topical reactions in some patients.

It is not understood why the excellent results described above have been achieved. However, the inventors recognize that there are similarities in the chemical structure of histamine and histone. Histone is a naturally occurring body substance that takes the form of a thin protein coat on genetic material. If the histone coat is damaged, for example by a virus, physical injury, or other factor, the damage may alter the properties of the histone coating enough that the genetic messages produced by the cell to reproduce itself or genetic messages of the cell acted upon by the human immune system are misinterpreted by the cell or by the immune system.

Although not wanting the invention to be limited by any particular theory or mechanism, the inventors believe that providing histamine locally to the area of the damage, rather than providing histamine systemically, may provide "building blocks" that result in natural regeneration of the histone coat on the cell and avoid misinterpretation of the cell's chemical messages, thereby avoiding undesirable responses by the immune system, or avoiding tumorous or cancerous cell growth. Perhaps the histamine acts at the genetic level in the vicinity of the histone coat, and performs one or more of the following functions:

(1) providing building blocks to repair the histone coat;
(2) providing stimulation of the genetic material, e.g., the basic chromosome within the cell, to react to trauma or damage of the cell to cause tissue repair; or
(3) reacting in such a way as to prevent a virus or the like from utilizing the genetic material within the cell to duplicate itself. (It should be appreciated that it is desirable to avoid systemic doses of histamine in the human body, because excessively high levels of histamine can cause a variety of problems and systems, some of which are specific to the gastrointestinal tract, and others of which can cause allergic reactions ranging from minor rashes to anaphylactic shock. Those skilled in the art certainly know that it would be undesirable to provide systemic treatments for localized lesions.)

While the invention has been described with reference to a number of particular embodiments thereof, those skilled in the art will be able to make various modifications to the described embodiment without departing from the true spirit and scope of the invention. For example, the above described composition may turn out to be useful for treatment of any topical or skin-type lesions, regardless of whether the lesions are ulcers, burns, virus-caused, or skin cancers. For example, the invention may be modified in either active ingredient level or by variation of base components to be useful for treatment of other herpetic lesions such as genital herpes or shingles. The invention also may be effective for other skin-type lesions, regardless of whether the lesions are ulcers, burns, virus-caused, or skin cancers. It should be appreciated that so-called "precursor IEP" substances or "prodrug" substances which are used in production of drugs might be useable in place of IEP. Such a prodrug may not itself be active, but may be modified by the body into an active drug that results in IEP locally.

What is claimed is:

1. A composition for topical treatment of herpes labialis lesions consisting essentially of a water soluble gel of a vinyl polymer mixed by blending approximately 0.00325 to 0.0067 percent by weight 1 H-imidazole-4-ethanamine, phosphate (IEP) uniformly with the gel.

2. The composition of claim 1 wherein the water soluble gel is an homogenous mixture of vinyl polymer, distilled water and dispersing agent.

3. A method of treating herpes labialis lesions, comprising the steps of blending approximately 0.00325 to 0.0067 percent by weight 1-H-imidazole-4-ethanamine, phosphate (IEP) uniformly with water soluble vinyl polymer gel, and topically applying the resulting blended composition to the lesions.

4. The method of claim 3 including applying the composition to the lesions approximately 5 times per day.